(12) United States Patent
Alvine et al.

(10) Patent No.: US 9,580,793 B2
(45) Date of Patent: Feb. 28, 2017

(54) SUBWAVELENGTH COATINGS AND METHODS FOR MAKING AND USING SAME

(71) Applicants: Kyle J. Alvine, Richland, WA (US); Bruce E. Bernacki, Kennewick, WA (US)

(72) Inventors: Kyle J. Alvine, Richland, WA (US); Bruce E. Bernacki, Kennewick, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 0 days.

(21) Appl. No.: 14/815,011

(22) Filed: Jul. 31, 2015

(65) Prior Publication Data

US 2016/0033685 A1 Feb. 4, 2016

Related U.S. Application Data

(60) Provisional application No. 62/032,400, filed on Aug. 1, 2014.

(51) Int. Cl.
| | |
|---|---|
| *C23C 14/04* | (2006.01) |
| *G02B 1/12* | (2006.01) |
| *G01N 33/543* | (2006.01) |
| *G02B 1/118* | (2015.01) |
| *C23C 14/02* | (2006.01) |

(52) U.S. Cl.
CPC .......... *C23C 14/046* (2013.01); *C23C 14/024* (2013.01); *G01N 33/54346* (2013.01); *G02B 1/118* (2013.01); *G02B 1/12* (2013.01); *Y10T 428/12104* (2015.01); *Y10T 428/249921* (2015.04)

(58) Field of Classification Search
None
See application file for complete search history.

(56) References Cited

U.S. PATENT DOCUMENTS

| | | |
|---|---|---|
| 5,229,339 A | 7/1993 | Pujari et al. |
| 6,979,704 B1 | 12/2005 | Mayer et al. |
| 8,512,588 B2 | 8/2013 | Tringe et al. |
| 8,599,486 B2 | 12/2013 | Najiminaini et al. |
| 8,905,559 B2 | 12/2014 | Kawauchi et al. |

(Continued)

FOREIGN PATENT DOCUMENTS

WO WO2010099805 * 9/2010 ............. C23C 14/04

OTHER PUBLICATIONS

T.G. Harvey, SPIE, vol. 3099, year 1997, pp. 76-82.*

(Continued)

*Primary Examiner* — Jiong-Ping Lu
(74) *Attorney, Agent, or Firm* — James D. Matheson (57) ABSTRACT

Methods are disclosed for forming subwavelength coatings for use in the UV, visible, or infrared part of the electromagnetic spectrum. A first material and a second material are deposited onto a substrate. The first material may include dielectric spheres of subwavelength size that self-assemble on the substrate to form a template or scaffold with subwavelength size voids between the spheres into which the second material is deposited or filled. First and second materials are heated on the substrate at a preselected temperature to form the subwavelength coating.

10 Claims, 10 Drawing Sheets

(56) References Cited

U.S. PATENT DOCUMENTS

| | | |
|---|---|---|
| 2009/0253227 A1 | 10/2009 | Defries et al. |
| 2010/0035039 A1 | 2/2010 | Jing et al. |
| 2011/0012086 A1 | 1/2011 | Tsakalakos et al. |
| 2011/0312080 A1* | 12/2011 | Hatton .................. A61L 27/40 435/289.1 |
| 2013/0045877 A1* | 2/2013 | Yap .................. G01N 33/54346 506/7 |
| 2013/0225760 A1 | 8/2013 | Jing et al. |
| 2013/0342898 A1 | 12/2013 | Alvine et al. |
| 2014/0177039 A1 | 6/2014 | Li et al. |

OTHER PUBLICATIONS

S.B. Quint and C. Pacholski, J. Mater. Chem. vol. 19, year 2009, pp. 5906-5908.*

W.A. Murray et al., Physical Review B, vol. 69, year 2004, pp. 165407-1 to 165407-7.*

S. Tsuji and H. Kawaguchi, Langmuir, vol. 21, year 2005, pp. 2434-2437.*

* cited by examiner

SUBWAVELENGTH COATINGS AND METHODS FOR MAKING AND USING SAME

CROSS REFERENCE TO RELATED APPLICATIONS

This is a non-provisional application that claims priority from U.S. Provisional Patent Application No. 62/032,400 filed 1 Aug. 2014, which reference is incorporated in its entirety herein.

STATEMENT REGARDING RIGHTS TO INVENTION MADE UNDER FEDERALLY-SPONSORED RESEARCH AND DEVELOPMENT

This invention was made with Government support under Contract DE-AC05-76RL 01830 awarded by the U.S. Department of Energy. The Government has certain rights in the invention.

FIELD OF THE INVENTION

The present invention relates generally to coatings and methods of making. More particularly, the present invention relates to subwavelength coatings and methods of making and applying the coatings. Subwavelength coatings of the present invention find use, for example, in window coatings, building envelope materials, paints, and devices such as scintillators, sensors, and security tags and seals used in thermal energy (e.g., solar) and electromagnetic energy management applications.

BACKGROUND OF THE INVENTION

Optical coatings such as Low-E coatings are used in windows to block solar heating via infrared electromagnetic radiation in buildings which improves energy efficiency by reducing cooling (HVAC) costs. New coatings and structures referred to as optical subwavelength coatings and structures (defined as acting in the UV, visible, or infrared), plasmonic, photonic, or metamaterials are now being developed by various research groups that are expected to allow tailored scattering of both visible and infrared light in ways not possible with previous coating technologies. The tailored spectral scattering response of new optical subwavelength coatings and structures is expected to go beyond what is currently possible with conventional thin films and coatings that have been limited by material properties that govern classical scattering at interfaces such as, for example, dielectric constants, roughness, and film thickness. For example, new subwavelength structures used as coatings may be expected to deliver substantial energy savings in buildings through spectral control of scattering of both visible and infrared light. One estimate suggests up to 30% of annual heating and cooling may be provided by dynamically controlling infrared transmission using selected window coatings. Additional savings may be possible by selective spectral control of window coatings that allows transmission of visible light while dynamically switching only the infrared light. However, current approaches for making subwavelength structures are not scalable or are prohibitively expensive to produce. Therefore these coatings cannot be applied to cover large areas (e.g., on buildings) or manufactured at a low cost for good market penetration. Accordingly, new processes are needed that enable production of subwavelength coatings that are scalable to very large areas, that have a high throughput, that can be manufactured at a low cost, and that provide spectrally selective properties in the UV, visible, and infrared portions of the electromagnetic spectrum. The present invention addresses these needs.

SUMMARY OF THE INVENTION

The present invention includes methods of forming subwavelength coatings with desired electromagnetic scattering in the infrared, UV, or visible. Subwavelength coatings of the present invention incorporate subwavelength objects of various sizes. The term "subwavelength" used herein means objects in the coating have dimensions less than a wavelength of electromagnetic radiation reflected or redirected by the coating. For example, a subwavelength structure that is subwavelength to visible light would include objects at or below about 300 nm. The term "coating" encompasses both films and coatings. The term "nanostructure" encompasses nanoscale objects including, e.g., nanospheres, nanorods, and nanoparticles having a dimension less than about 500 nanometers (nm), or less than about 200 nm, or less than about 100 nm, or less than about 50 nm, or less than about 20 nm. Nanostructures can be substantially homogeneous in material properties. However, in other embodiments, the nanostructures can be heterogeneous. Nanostructures can be substantially crystalline (monocrystalline or polycrystalline), amorphous, or include both crystalline and amorphous properties. The term "microstructure" encompasses microscale objects including, e.g., spheres, rods and particles having a dimension less than about 30 microns.

The present invention includes coatings on substrates having one or more layers of selected materials with controlled thicknesses as small as a monolayer.

In one embodiment of the present invention, a first material and a second material are deposited onto a substrate. The terms "deposit" and "deposition" used herein may mean to emplace, to introduce, or to place. In some embodiments, "wet deposition" is described herein in which nanostructures or microstructures are deposited directly to substrates in solvents or aqueous solutions without need for vacuum-processing techniques such as, for example, vacuum-lithography (e.g., e-beam or ion beam) or vacuum-deposition.

The first material deposited on the substrate may include dielectric spheres of a subwavelength size that self-assemble on the substrate to form a template or scaffold on the substrate. Here, the subwavelength spheres have a diameter less than or equal to about two thirds of the wavelength in the UV or visible spectrum of interest. For example, for a coating designed to operate in the visible spectrum at 500 nm, subwavelength spheres would be no larger than about 333 nm in diameter. For a coating designed to operate in the IR spectrum at 8 microns, subwavelength spheres would be no larger than about 5.3 microns in diameter. The term "self-assemble" means the nanoscale or micron-scale spheres arrange themselves in a quasi-organized structure or pattern on the substrate. The term "template" refers to a base layer or scaffold comprised of nanospheres or microspheres in a close-packing arrangement or near close-packing arrangement on the substrate. The term "close-packing" means the nanospheres or microspheres are arranged in a layer or layers on the substrate in which the nearest neighbor particles are either touching or nearly touching.

The template or scaffold formed by the particles or spheres of the first material may include subwavelength-sized voids or depressions ("valleys") positioned between the spheres into which the second material is deposited or filled. The substrate containing first and second materials in the selected arrangement may be heated at a preselected temperature to dry or sinter the structure that yields the final subwavelength coating. In this embodiment, the method does not employ vacuum deposition. As described above, the dielectric spheres of the first material may include an average size (diameter) smaller than about two-thirds of a selected wavelength within the UV, visible, or infrared part of the electromagnetic spectrum.

In one embodiment, the subwavelength coating includes a quasi-periodic subwavelength mesh structure or coating of the second material that extends in at least two dimensions substantially conformal to the substrate.

In some embodiments, the mesh structure or coating of the second material may include a dielectric or a metal, but is not limited thereto.

In one embodiment, the first material is deposited on the substrate by drying a solution containing the first material. The solution may be comprised of the dielectric spheres of subwavelength size that are suspended in the liquid.

In some embodiments, the dielectric spheres may include a ceramic material, a polymer material, or a metal oxide. Polymer materials may include, but are not limited to, for example, polystyrene, poly-methyl methacrylate, or cross-linked poly(styrene/divinylbenzene) (P[S/DVB]), melamine, polyactide, or combinations thereof. Ceramic materials selected as first materials or second materials may include, but are not limited to, for example, silica, alumina, titania, or combinations of these materials. Dielectrics may also include metal oxides with a metal-insulator transition such as vanadium oxide.

Ceramics, metals, and polymer materials selected as first materials or second materials can be functionalized with ligands or combined with a surfactant for enhanced dispersion in a solvent or aqueous solution for deposition.

In one embodiment, the spheres have a substantially similar diameter from a range between about 50 nm to about 15 microns. In one embodiment, the average diameter of the spheres is set by a wavelength of electromagnetic radiation within the UV, visible, or infrared part of the electromagnetic spectrum.

In one embodiment, the second material is deposited onto the template or scaffold by drying from a solution of sinterable metal nanoparticles which are sphere-like or rod-like in structure and having an approximate diameter size selected from a range between about 1 nm and about 100 nm. Sinterable metal nanoparticles may have a maximum average dimension smaller than at least one half of a sphere diameter of the first material.

The subwavelength mesh coating can exhibit at least one resonant response to reflect, transmit, or absorb a select band of electromagnetic, UV, visible, or infrared radiation when incident thereon.

In one embodiment, the second material is deposited onto the first material template or scaffold by drying from a solution of the second material or cooling from a melt of a dielectric material or emulsion of dielectric materials of the second material, wherein the second material has a different dielectric constant than the template or scaffold and is deposited within voids or valleys between the particles or objects of the first material to form a substantially lateral extending quasi-periodic varying dielectric mesh or pattern.

In one embodiment, the second material may be an emulsion of dielectric materials, wherein the particles have an average diameter selected from a range between about 1 nm and about 100 nm, wherein the second material average diameter is chosen to be smaller than one half of a sphere diameter of the first material.

The subwavelength dielectric mesh affects transmission or reflection of incident electromagnetic radiation in UV, visible, or infrared light such that selected bands of wavelengths of the electromagnetic radiation are blocked or propagate through or along the subwavelength coating.

In one embodiment, the substrate is flexible. In another embodiment, the substrate is non-flat or non-planar. The non-flat or non-planar substrate may be, but is not limited to, an individual fiber or textile.

In one embodiment, the method further includes interconnected stack layers of the subwavelength coating.

In one embodiment, the dielectric spheres of the first material have a poly-modal size distribution having at least two different average diameter groupings.

In one embodiment, the dielectric spheres are etched to reduce their size after deposition on the substrate to form a template or scaffold.

The template or scaffold may be replicated from a subwavelength mold by embossing, contact printing, or UV curving.

The subwavelength coating can be applied as a window or window-like device for use in structures that allow transmission, reflection, or adsorption of electromagnetic radiation in the UV, visible, or infrared part of the electromagnetic spectrum.

The subwavelength coating can also be applied to a device utilizing electromagnetic radiation in the UV, visible, or infrared part of the electromagnetic spectrum for power generation or dissipation. Further, the subwavelength coating can be applied for use as part of an identifying or counterfeit resistant tag or seal, for use as an interface between two separate materials, for use in sensor for sensing of electromagnetic radiation, or a chemical, biological, or neutron signature, or for use in a structure to allow transmission, reflection, or adsorption of electromagnetic radiation in the UV, visible, or infrared part of the electromagnetic spectrum as a building envelope, a mirror-like device, or a wearable device.

In another embodiment of the present invention, a method of forming a subwavelength coating for use in the UV, visible, or infrared portion of the electromagnetic spectrum is disclosed. The method includes depositing at least a first material and a second material onto a substrate, wherein the first material includes dielectric objects of subwavelength size that self-assemble on the substrate to form a template or scaffold with subwavelength-sized voids and valleys between the objects into which the second material is deposited or filled. The method also includes heating the first and second materials on the substrate at a preselected temperature to form the subwavelength coating. In one embodiment, the subwavelength dielectric objects may be non-spherical.

In another embodiment of the present invention, a method of forming a subwavelength coating for use in the UV, visible, or infrared part of the electromagnetic spectrum. The method includes depositing at least a first dielectric material of subwavelength size spheres on a substrate to self-assemble to form a sacrificial template or scaffold. The method may also include etching the spheres of the first material to increase the size of voids between the spheres, and depositing a second metal or dielectric material on the substrate via vacuum deposition in regions not blocked by the presence of objects of the first material. The method further includes removing the sacrificial template or scaffold to create a quasi-periodic subwavelength metal or dielectric mesh formed by the deposition of the second material on the substrate through gaps in the template or scaffold.

DETAILED DESCRIPTION

The present invention includes a process for low-cost fabrication of nanostructured or microstructured subwavelength coatings and devices. In the following description, embodiments of the present invention are shown and described by way of illustration of the best mode contemplated for carrying out the invention. It will be clear that the invention is susceptible of various modifications and alternative constructions. The present invention covers all modifications, alternative constructions, and equivalents falling within the spirit and scope of the invention as defined in the claims. Therefore the description should be seen as illustrative and not limiting.

Process-I

Wet Deposition Fabrication of Subwavelength Coatings

Figure 1:
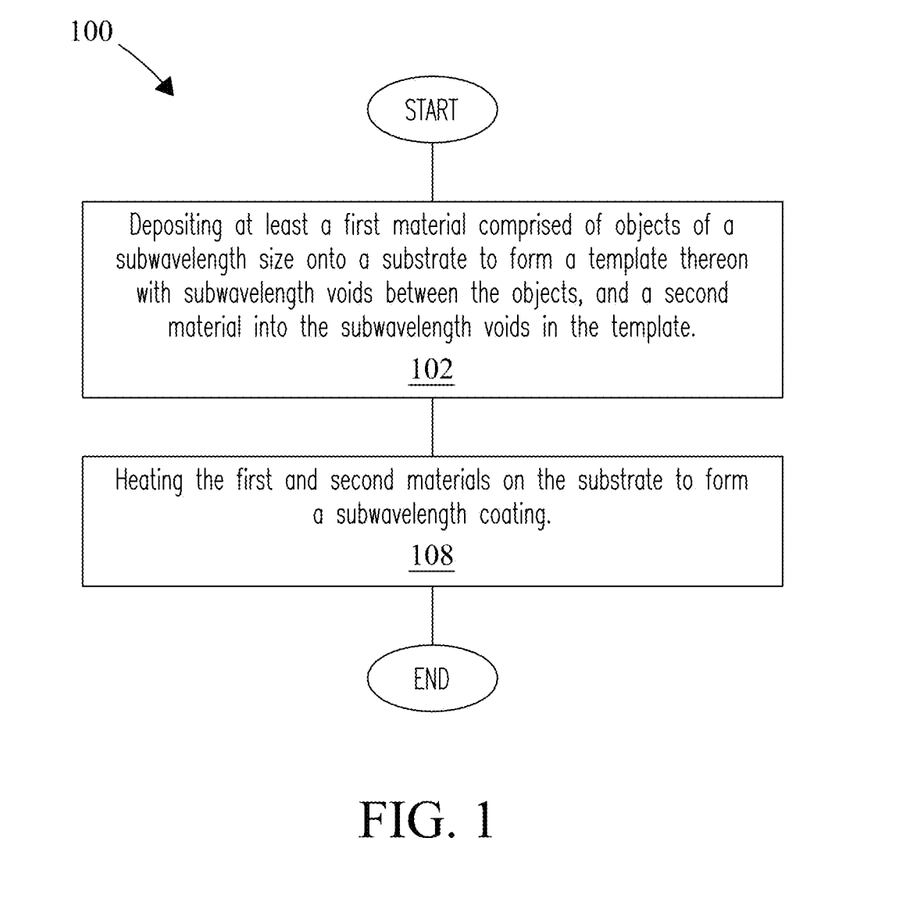
FIG. 1 presents an exemplary process for fabrication of subwavelength coatings of the present invention.

FIG. 1 illustrates an exemplary process 100 for fabrication of subwavelength coatings of the present invention. {START}. In exemplary steps {102} {104}, at least a first material 4 comprised of nanostructured or microstructured objects 4 and a second material 6 comprised of nanoparticles 6 of a subwavelength size may be deposited onto a substrate 2. Substrates 2 are not limited.

In a preferred embodiment, nanostructures or microstructures 4 of the first material may be nanospheres or microspheres. In another embodiment, nanostructures 4 of the first material may be nanoparticles. Nanostructures or microstructures 4 of the first material and nanoparticles 6 of the second material may be delivered, for example, from a solution, as detailed further herein. In some embodiments, the solution may be an aqueous solution that may include surfactants. In some embodiments, the solution may include one or more selected organic solvents. In some embodiments, the first material deposited to the substrate may be a polymer having no sphere or particle form that is delivered in a solution. Concentrations of nanostructures or microstructures 4 and nanoparticles 6 in the carrier solutions are not limited. Nanostructures or microstructures 4 of the first material in solution may have concentrations selected between about 0.5% to about 20% solids by weight.

In some embodiments, deposition steps {102} {104} may be performed consecutively.

In some embodiments, deposition steps {102} {104} may be performed simultaneously, for example, on different areas of the substrate 2. For example, a first deposition step {102} may take place on an uncoated (or first) section of the substrate 2, and a second deposition step {104} may take place on a different section of substrate 2, e.g., downstream from the first section, where the first coating step {102} has already taken place. No limitations are intended.

Nanostructures or microstructures 4 when deposited or applied self-assemble in a selected close-packing arrangement or near close-packing arrangement, which forms a template or scaffold 10 on the substrate 2. The template or scaffold 10 may include voids 8 or valleys of a subwavelength size positioned between the nanostructures or microstructures 4. Nanoparticles 6 of the second material deposit into or fill voids 8 and valleys between the nanostructures or microstructures 4.

As will be appreciated by those of ordinary skill in the art, self-assembly of nanostructures or microstructures that form the template or scaffold on the substrate is influenced by various deposition parameters including, for example, solution deposition volume, solution deposition rate, nanoparticle concentrations, carrier solvents, solution wetting behavior of the substrate (i.e., the spreading of the solution on underlying substrate materials and associated solution contact angles), and drying and sintering temperatures. Control of these various parameters defines how spheres and particles in solution spread over the substrate and deposit to form the template structure. Control of these parameters also mitigates formation of defects such as holes, or areas of missing deposition coverage, i.e., where particles are missing in the template structure or areas where particle multilayers or particle islands exist in the template structure.

In another optional step {106}, the substrate 2 now containing nanostructures or microstructures 4 of the first material and nanoparticles 6 of the second material may be heated at preselected temperatures to remove solution solvents and to dry the first and second materials on the substrate 2. Drying temperatures are not limited. Exemplary drying temperatures may be selected between about room temperature (20° C.) to about 100° C. Higher temperatures may also be employed. Thus, no limitations are intended.

In another optional step {108}, the substrate 2 containing nanostructures or microstructures 4 of the first material and nanoparticles 6 of the second material may be heated at a preselected temperature to sinter the first and second materials that forms the subwavelength coating. Exemplary sintering temperatures may be selected between about room temperature (20° C.) to about 280° C. In a preferred embodiment, sintering temperature may be about 250° C. However, sintering temperatures are not intended to be limited. For example, as will be appreciated by those of ordinary skill in the art, sintering temperatures selected for use depend in part on the second materials selected for use in the subwavelength coatings. Thus, no limitations are intended by exemplary temperatures described herein. The subwavelength coating once formed may be employed to reflect or direct electromagnetic radiation in the UV, visible, or infrared.

In various embodiments, nanostructures or microstructures 4 of the first material may include a dielectric material, polymers such as polystyrene, silica, or a metal oxide with a metal insulator transition such as vanadium oxide described herein.

In various embodiments, second material nanoparticles may include a noble metal such as silver or gold, or a metal oxide with a metal-insulator transition such as vanadium oxide.

In some embodiments, the subwavelength coating may exhibit plasmonic properties and be comprised of silica nanospheres or microspheres as a first material and nanoparticles of silver or gold as a second material.

In some embodiments, the subwavelength coating may exhibit photonic properties and be comprised of nanospheres or microspheres of a dielectric material such as polystyrene as the first material and a second material with a different dielectric constant than the first material.

System for Fabrication

Figure 2:
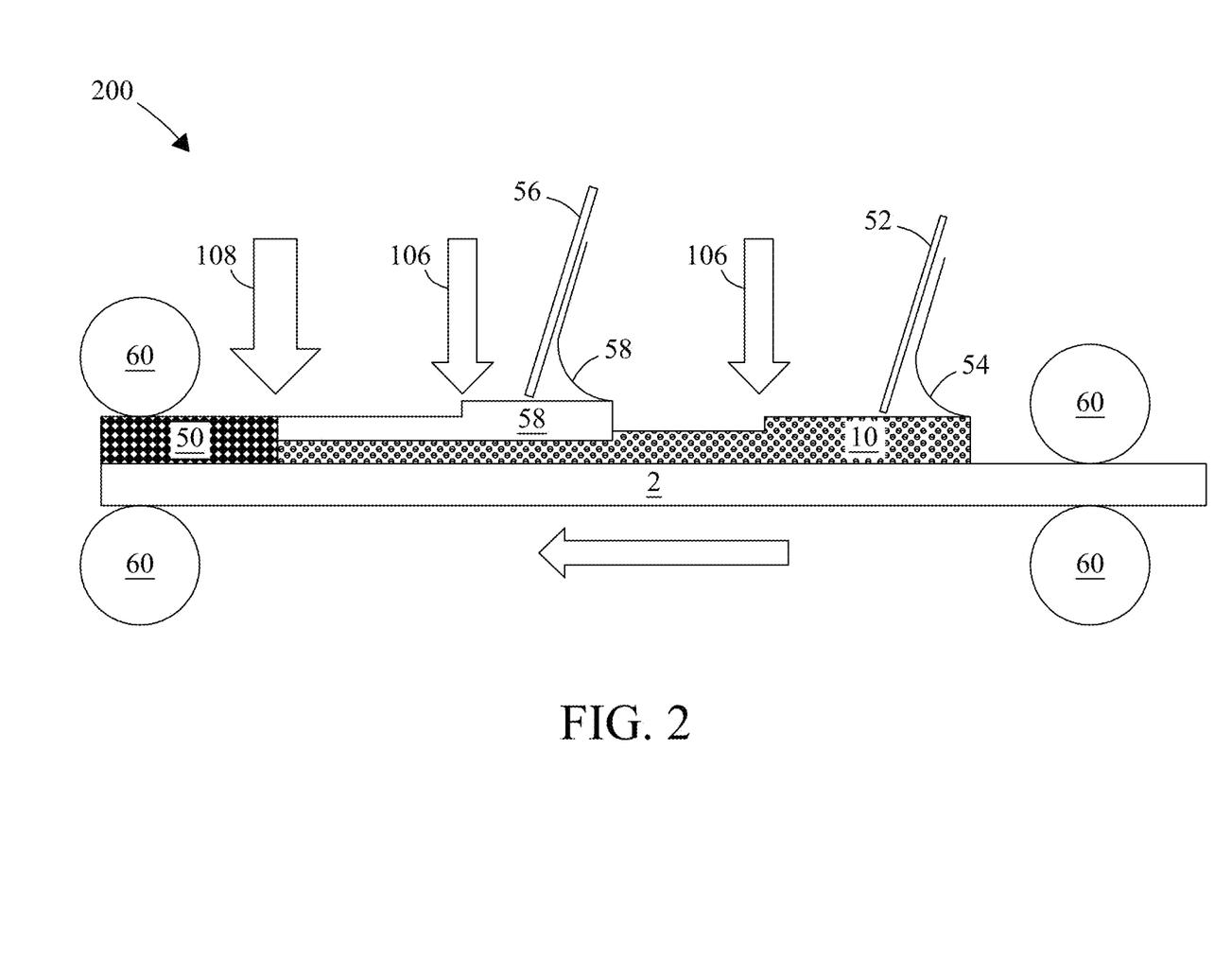
FIG. 2 illustrates an exemplary system for fabricating subwavelength coatings of the present invention.

FIG. 2 illustrates an exemplary system 200 of a linear, continuous (e.g., web-based) coating design for fabrication of subwavelength coatings of the present invention. System components and operation are detailed hereafter.

In the figure, system 200 may include a first delivery blade 52, head, or nozzle that deposits or delivers a first solution 54 containing nanostructures or microstructures (e.g., nanospheres, nanoparticles, or microspheres) (described further in reference to FIG. 3A) of a first material (e.g., in water or other solvent) to the substrate 2 that coats or partially coats the substrate and forms a template or scaffold 10. Cleaning and pre-treatment of the substrate may be employed to improve wetting of the substrate by the deposition solutions. Deposition may proceed as follows. The first blade 52 (head or nozzle) may be positioned in contact with a first solution reservoir (not shown) a selected distance (e.g., 100 microns) above the forward-moving substrate 2. The first blade 52 in contact with a first solution reservoir (not shown) may deliver the solution 54 containing the nanospheres or microspheres onto the moving substrate 2. The solution 54 may contain, as an example, a 5% by weight concentration of 170 nm diameter silica nanoparticles (Bangs Laboratories, Inc., Fishers, Ind., USA) in aqueous solution that is deposited to the substrate 2. Substrates 2 may be kept in forward motion with rollers 60 or like devices.

Figure 3A:
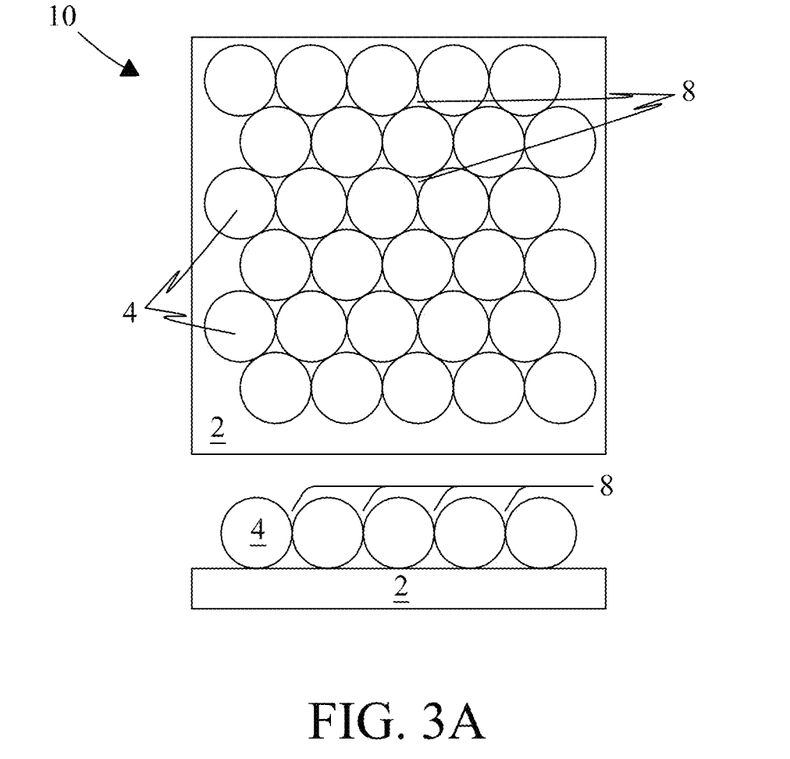
FIGS. 3A-3F show coated structures in the process of FIG. 1.

Following delivery of the first solution 54, the substrate 2 containing wet nanostructures or microstructures may be dried (106) with, for example, a heat lamp, a drier, an oven, or other heating device at a selected temperature to remove the solvent (e.g., water) and cause the nanospheres or microspheres to self-assemble in the close-packing or near close-packing arrangement, forming a monolayer (or multilayer) template or scaffold 10 of first nanostructures or microstructures on the substrate 2 (described further hereafter in reference to FIG. 3A). As an example, heat may be delivered via a 500-Watt halogen lamp positioned about 6 inches (15.2 cm) from the substrate 2 at about 70% power as the substrate 2 moves forward at a rate of about 5 mm per second. Faster times, solutions with different particle concentrations, and heat lamp power may be selected. No limitations are intended.

A second delivery blade 56 or head in contact with a second solution reservoir (not shown) may be positioned downline from the first blade 52 a selected distance (e.g., 100 microns) above the moving substrate 2 that deposits or deliver a second solution 58 containing nanoparticles of a second material (e.g., in a hydrocarbon solvent or co-solvents) as a second wet layer onto the moving substrate 2. As an example, the second solution may contain silver (Ag) nanoparticles (Sigma-Aldrich, St. Louis, Mo., USA) of a diameter less than or equal to about 10 nm at a concentration of about 14% by weight after dilution in a solution containing two (2) parts heptane and one (1) part tetradecane. The solution 58 may be delivered to the template 10 on the substrate 2 moving at a rate of, for example, 5 mm per second, which introduces or fills subwavelength voids (not shown) between the template nanostructures or microstructures with the second nanoparticles in the template or scaffold 10 (described further hereafter in reference to FIG. 3C).

Following delivery of the second material nanoparticles (e.g., metals), the substrate 2 may again be dried (106) to remove residual solvents and to bind or trap nanoparticles of the second material within the voids between the first nanoparticles in the template or scaffold 10. Sintering (108) of the second materials at selected temperatures forms a subwavelength mesh ("fish-net") coating 50. For example, sintering of silver nanoparticles may be performed at a selected temperature (e.g., 250° C.) for a selected time (e.g., ½ hour) which turns the nanoparticles into a percolated, conductive metal mesh.

Substrates

Substrates suitable for use include, but are not limited to, for example, metals, metal alloys, metal oxides, silicon oxides, glass, glass-containing materials, low-E glass, ceramics, silicon carbide (SiC), polyimides (e.g., KAPTON®), polyamides (e.g., NYLON®), polymers, polyesters, plastics, and combinations of these materials. No limitations are intended.

In various embodiments, substrate metals may include, for example, aluminum, copper, and iron.

In various embodiments, substrate metal alloys may include, for example, alloys of steel, copper, aluminum, iron, and combinations of these various metals and metal alloys.

In various embodiments, glass-containing materials may include, but are not limited to, e.g., fused silica glasses, borosilicate glasses.

In various embodiments, ceramics may include, but are not limited to, e.g., alumina, titania, sapphire, yttria, yttrium-stabilized zirconium (YSZ), silicon carbide (SiC), and combinations of these ceramics.

In various embodiments, polymers may include, but are not limited to, e.g., acrylics, polyesters, polystyrenes, polyethylenes, polycarbonates, and combinations thereof.

In some embodiments, flexible substrates may be used.

In some embodiments, rigid substrates may be used.

All substrates that can be coated with subwavelength coatings of the present invention may be used without limitation. No limitations are intended.

First Materials

First material nanospheres, microspheres (or nanoparticles and microparticles) may be comprised of selected materials including, but not limited to, for example, dielectric materials including dielectric polymers (e.g., polystyrene), silica, semiconductors, and metal oxides with metal-oxide transitions such as vanadium oxide.

Concentration of nanospheres, microspheres, and nanoparticles of the first material in solution may be selected between about 0.5% to about 25% by weight.

Nanospheres or microspheres of the first material selected for the template or scaffold may include various selected sizes.

In some embodiments, particles of the first material may include a size (diameter) selected between about 20 nm to about 200 nm that provides a selected optical response.

In some embodiments, particles of the first material may include a size (diameter) selected between about 100 nm to about 300 nm that provides a selected optical response.

In some embodiments, particles of the first material may include a size (diameter) selected between about 200 nm to about 500 nm that provides a selected optical response.

In some embodiments, particles of the first material may include a size (diameter) greater than about 500 nm that provides a selected optical response.

In some embodiments, particles of the first material may include a size (diameter) selected between about 1 micron to about 20 microns. No limitations are intended.

Second Materials

In various embodiments, nanoparticles of the second material may comprise metals including, but not limited to, for example, silver (Ag), gold (Au), aluminum (Al), metal oxides, and combinations of these materials.

In some embodiments, nanoparticles of the second material may comprise metal oxides including, but not limited to, for example, titania ($TiO_2$), alumina ($Al_2O_3$), nickel oxides, and materials with a metal-insulator transition such as vanadium oxide, or semiconductors.

In some embodiments, second materials may include polymers described herein that do not have a particle form.

Concentration of second material in solution may be selected between about 1% to about 70% by weight.

Nanoparticles of the second material may have a size with a dimension smaller than those of the first nanospheres or microspheres in the template or scaffold. Second material nanoparticles deposit within the voids positioned between the nanospheres and microspheres in the template or scaffold.

In some embodiments, nanoparticles of the second material include a size (diameter) between about 1 nm to about 100 nm.

In some embodiments, nanoparticles of the second material include a size (diameter) between about 5 nm to about 10 nm.

In some embodiments, nanoparticles of the second material include a size (diameter) between about 10 nm to about 20 nm.

In some embodiments, nanoparticles of the second material include a size (diameter) between about 20 nm to about 30 nm.

In some embodiments, nanoparticles of the second material include a size (diameter) between about 30 nm to about 40 nm.

In some embodiments, nanoparticles of the second material include a size (diameter) between about 40 nm to about 50 nm.

In some embodiments, nanoparticles of the second material include a size (diameter) between about 10 nm to about 50 nm. However, no limitations are intended.

Solvents

Solvents suitable for use include, but are not limited to, water, hexanes, heptanes, octanes, decanes, tetradecanes, other hydrocarbons, fluorocarbons, and combinations of these solvents. In some embodiments, solvents may include selected surfactants. Solvents selected for use in carrier solutions may vary depending on the first and second particles selected for use in the subwavelength coatings and temperatures selected for sintering the coating substrates. For example, solvents have a boiling point sufficiently high such that the solvent remains in the coating until the second particles (e.g., metal nanoparticles) sinter to the first particles (e.g., silica nanospheres) in the template of the subwavelength coating. Thus, no limitations are intended.

Coating Processes

Substrates may be coated with processes including, but not limited to, for example, web-coating, roll-to-roll coating, painting, spray-painting, spray-coating, drop-coating, dip-coating, spin-coating, air-brushing, air-coating, including combinations of these various methods. No limitations are intended.

Formation of Subwavelength Mesh (Fish-Net) Structures—(I)

FIG. 3A illustrates an exemplary monolayer template or scaffold that forms on a substrate 2 following a first deposition step in the process of the present invention described previously in reference to FIG. 1. In the figure, the template or scaffold includes nanospheres or microspheres 4 of a first material [e.g., polystyrene (PS)] that self-assemble in a close-packing arrangement on the substrate 2. The template includes voids 6 positioned between the close-packed nanospheres or microspheres 4.

Figure 3B:
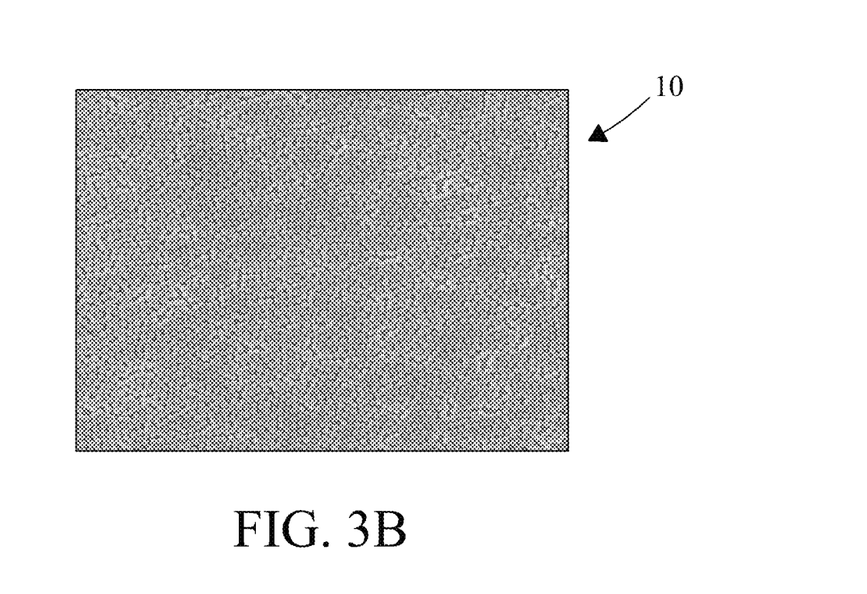

FIG. 3B is a Scanning Electron Micrograph (SEM) image showing an exemplary template 10 formed following deposition and self-assembly of representative first material (i.e., silica) nanospheres 4. Nanospheres are of a uniform or single particle size. The SEM image shows an approximate close sphere-sphere packing of nanospheres 4 in the template.

Figure 3C:
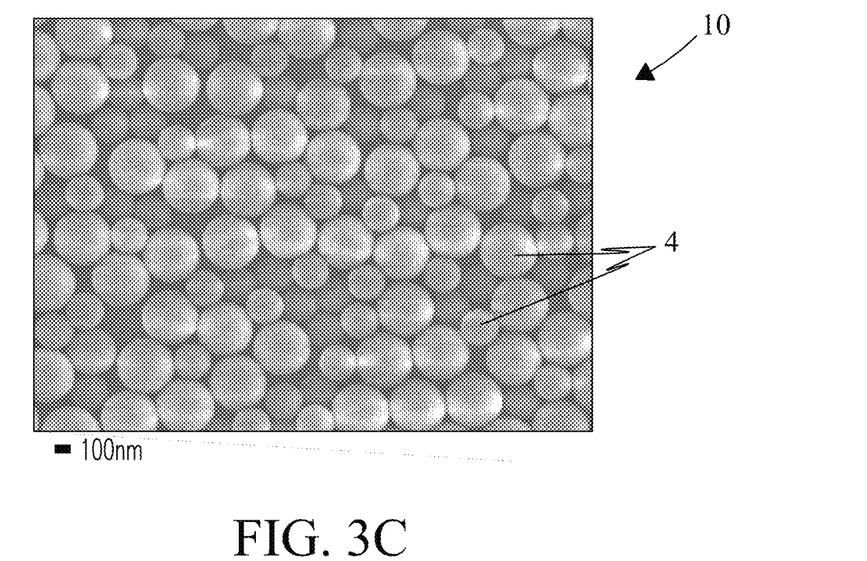

FIG. 3C is an SEM image showing a template or scaffold 10 formed following deposition and self-assembly of representative first material (i.e., silica) nanospheres or microspheres 4. In the instant embodiment, nanospheres 4 have a poly-modal size distribution with at least two different average sizes or diameters. Number of different particle sizes selected for a coating is not limited. The SEM image shows an approximate close sphere-sphere packing of nanospheres 4 in the template.

Figure 3D:
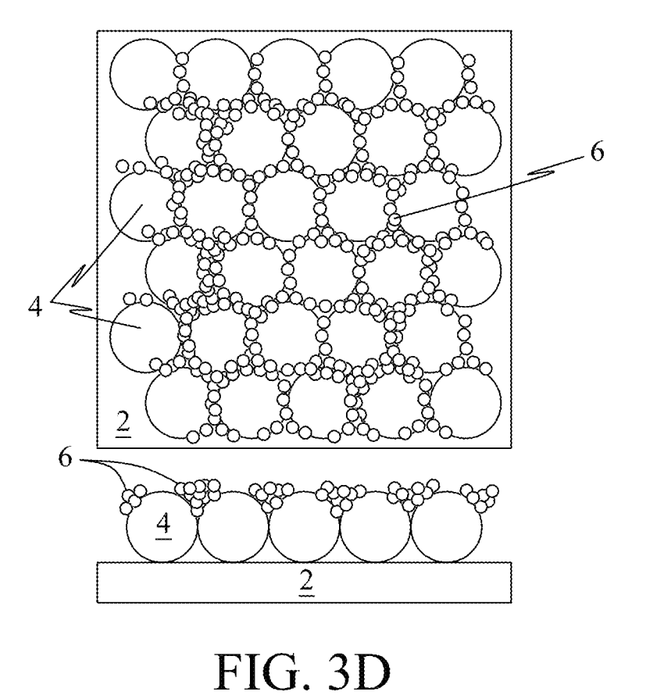

FIG. 3D illustrates the structure of the coated substrate 2 following deposition of second material nanoparticles 6 described previously in reference to FIG. 1. As shown, nanoparticles 6 of the second material (e.g., silver or gold) deposit into and fill voids 8 and valleys positioned between nanospheres 4 in the template or scaffold (FIG. 3A).

Figure 3E:
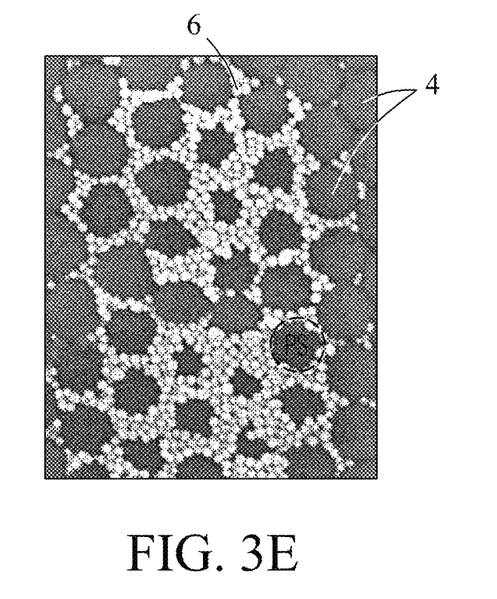

FIG. 3E is an SEM image showing a typical coated substrate 2 following deposition of second material (e.g., silver) nanoparticles 6. As shown, the nanoparticles 6 are present in the voids 8 positioned between the nanospheres 4 (e.g., polystyrene) in the template or scaffold (FIG. 3A).

Following deposition of second material nanoparticles 6, the coated substrate 2 may be heated at a selected temperature to sinter the first material nanospheres 4 and second material nanoparticles 6, which forms the subwavelength mesh coating (FIG. 3E).

Figure 3F:
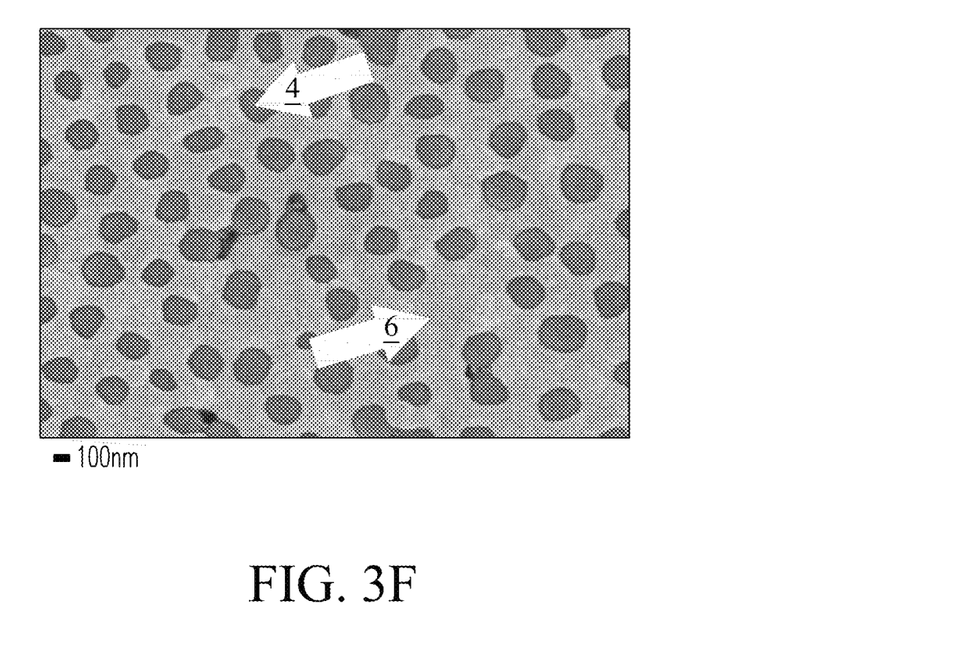

FIG. 3F is an SEM image showing a representative (e.g., plasmonic) subwavelength coating 50 of the present invention showing its characteristic quasi-periodic mesh (or "fish-net") structure. The subwavelength coating also includes a substantially uniform thickness.

Wavelength Scattering as a Function of Particle Size

Figure 4:
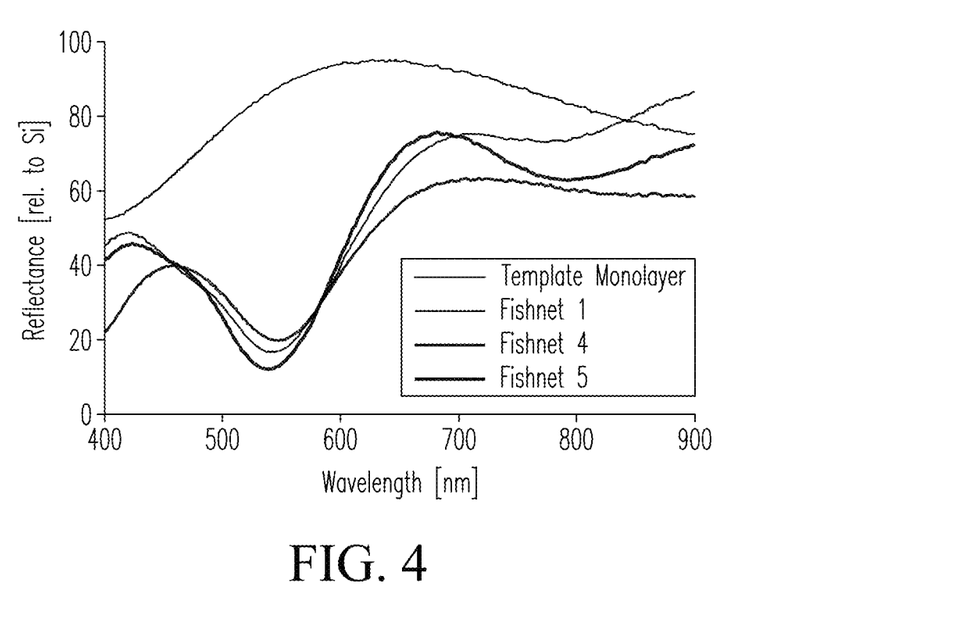
FIG. 4 compares reflectance values of an exemplary template and representative subwavelength coatings prepared in accordance with the present invention.

FIG. 4 compares reflectance values of an exemplary monolayer (first material) template comprised of silica nanospheres and representative subwavelength coatings formed with metal (second material) nanoparticles that result in resonant behavior. The terms "resonance" and "resonant" used herein mean the coatings transmit, absorb, or reflect selected wavelengths of electromagnetic radiation incident upon the coating. As shown in the figure, the template comprised of only silica nanospheres shows no resonance, whereas the subwavelength coatings with their quasi-periodic patterns of first and second materials are resonant structures that exhibit various and different resonance behaviors as a function of wavelength. In the figure, for example, the present subwavelength coatings exhibit a characteristic resonance at about 550 nm.

Resonance (absorption, transmission, or reflection) behavior can be tailored for selected applications based on choices of the first and second materials and other factors including, but not limited to, for example, particle size, particle concentration, particle distribution, and coating thickness. TABLE 1 shows resonances for representative subwavelength coatings of the present invention based on the selected particle size for selected applications.

TABLE 1

| Coating Type | Particle 1 | Particle Size (nm) | Particle 2 | Particle Size (nm) | Resonance Region |
|---|---|---|---|---|---|
| Plasmonic | Silica | 20-200 | Au | 1-30 | UV-VIS |
| Plasmonic | Silica | 200-20000 | Au | 1-100 | IR |
| Plasmonic | Silica | 20-200 | Ag | 1-30 | UV-VIS |
| Plasmonic | Silica | 200-20000 | Ag | 1-100 | IR |
| Photonic | Silica | 20-200 | Polymer | NA | UV-VIS |
| Photonic | Silica | 200-20000 | Polymer | NA | IR |
| Photonic | Polymer | 20-200 | Polymer | NA | UV-VIS |
| Photonic | Silica | 200-20000 | Polymer | NA | IR |
| Photonic | Silica | 200-20000 | Ceramic | 1-100 | IR |

Subwavelength coatings of the present invention with their first and second materials provide beneficial scattering effects not possible with current optical coatings. For example, in some embodiments, coatings may exhibit a plasmonic effect, in which there is a resonant absorption, transmission, or reflection over a selected range of wavelengths. The range of wavelengths may be selected based on the structure of the subwavelength coating rather than the specific material properties such as molecular absorption.

Another example is a photonic band gap coating where the structure of the subwavelength coating permits allowed or prohibited bands of wavelengths to propagate through or along the coating. Here, resonant properties are again dependent on the subwavelength structure and geometry rather than the material properties such as molecular absorption alone.

In some embodiments, subwavelength coating structures of the present invention may provide unique scattering used to manage infrared (IR) energy, for example, by selectively blocking infrared solar irradiance while accepting visible light with the plasmonic structures.

In some embodiments, a photonic structure may be used to preferentially allow radiative IR cooling in a transparent atmospheric window within a wavelength range of between about 8 to about 13 microns among other applications.

Process-II

Figure 5:
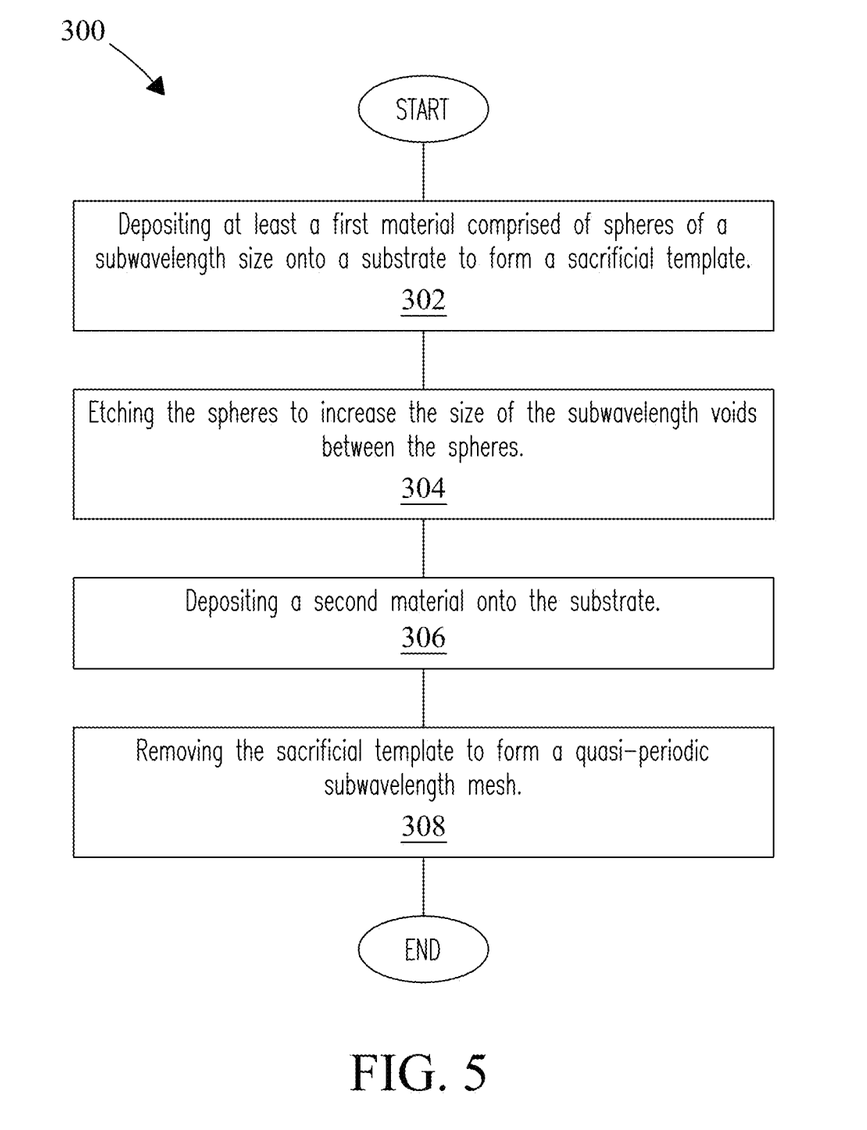
FIG. 5 presents another exemplary process for fabrication of subwavelength coatings of the present invention.

Combined Wet Deposition and Vacuum-Deposition Fabrication of Subwavelength Coatings FIG. 5 presents another exemplary process 300 for fabrication of subwavelength coatings 50 of the present invention suitable for use in scattering of electromagnetic radiation in the UV, visible, or infrared portions of the electromagnetic spectrum. Subwavelength coatings of the present invention may include a quasi-periodic mesh (or "fish-net") structure. {START}. In one exemplary step {302}, a first material comprised of nanostructures (e.g., nanospheres or nanoparticles) of a subwavelength size may be deposited to form a sacrificial template or scaffold (described in reference to FIG. 6A) on a substrate 2. Substrates are not limited as described previously herein.

In some embodiments, the nanostructures may be nanospheres. In some embodiments, the nanostructures may be nanoparticles. In some embodiments, the nanostructures may be comprised of a dielectric material.

In various embodiments, first material nanostructures or microstructures may include a dielectric material such as polystyrene or other selected polymers, silica, or metal oxides.

First materials (e.g., nanospheres and microspheres or polymer materials) and may be deposited, for example, from a solution. In some embodiments, the solution may be an aqueous solution. In some embodiments, the solution may include one or more selected organic solvents. Concentrations of subwavelength objects in solution are not limited. Concentrations of subwavelength objects may vary significantly from about 1% to about 20% by weight. Concentrations are linked at least in part to the rate or speed at which deposition occurs. As an example, a monolayer of quasi-monodisperse dielectric nanospheres of polystyrene may be deposited from an aqueous solution of polystyrene (~10% solids) onto the substrate at one speed, while a higher or lower concentration may be used if deposition is performed at a faster speed. Results may vary depending on the selected method of deposition. Subwavelength objects when deposited and dried on a substrate can self-assemble naturally in a close-packing or near close-packing arrangement, which forms a template or scaffold on the substrate. Templates or scaffolds do not need to be used immediately. Templates and scaffolds may be formed for later or subsequent use.

For example, in the case of silica or polystyrene nanospheres, the spheres can self-assemble via hard-sphere packing into a monolayer with a quasi-periodic hexagonal close packing arrangement in which nearest neighbors touch. A multi-layer close-packing arrangement is also possible. The template or scaffold may include voids and valleys of a subwavelength size (described hereafter in reference to FIG. 6A) positioned between and around the nanostructures. The nanostructures may be dried as described previously in reference to FIG. 1 and FIG. 2. In the exemplary embodiment, the polystyrene nanospheres may be heated after drying at a temperature slightly below or at a range of temperatures above the glass transition temperature (e.g. about 100° C.) for a time between about 1 minute to about 5 minutes to increase particle adhesion to the substrate. Times are not limited and depend at least in part on the temperatures selected. For example, the process may take hours at temperatures slightly below the glass transition temperature, while it may take only seconds at temperatures much above the glass transition temperature.

In another optional step {304}, first material nanostructures on the substrate may be etched in a plasma (e.g., oxygen ($O_2$), argon (Ar), or other suitable plasma) to increase the size of the voids between the nanospheres by isotropically reducing the size of the nanospheres or nanoscale-sized objects of the first material.

In another exemplary step {306}, a second material comprised of metal or dielectric may be deposited onto the substrate via shadow deposition where nanoscale-sized objects of the first material shadow selected areas of the substrate from the deposition of the second material. The second material may be deposited via vacuum-deposition methods including, but not limited to, for example, magnetron-sputter deposition or thermal evaporation onto the nanospheres or nanoscale objects and exposed portions of the substrate wherein nanoscale objects were previously deposited on the substrate. In various embodiments, the second material may include a noble metal such as silver or gold, or a thermochromic metal oxide such as vanadium oxide.

In some embodiments, deposition does not proceed from the source to the sample along a straight line (i.e., "line of sight").

In some embodiments, "line-of-sight" deposition may be performed in which a deposition angle between about 30 degrees to about 90 degrees relative to the sample normal or sample surface may be selected, measured from the plane of the substrate. A structure of the second material is formed on the substrate that includes subwavelength-sized ellipsoidal or circular holes created by shadowing of the first material template structures that depends in part on the selected angle of deposition. For example, deposition that proceeds normal to the sample surface forms approximately circular holes, while deposition at approximately 60 degrees from the surface normal forms ellipsoidal holes. The long axis is approximately aligned along the projection of the sputter angle onto the substrate. Deposition results in structures with an anisotropic optical response that can vary with angle and polarization. The second material may include an index of refraction that is different than that of the first material.

In another exemplary step {308}, subwavelength objects in the sacrificial template may be removed from the substrate after deposition of the second material to form, for example, a coating with subwavelength ellipsoidal holes. As described above, subwavelength ellipsoidal holes may be created by shadow deposition of the second material onto the subwavelength objects of the first material. Shadow deposition yields the quasi-periodic subwavelength metal or dielectric mesh coating on the substrate. Holes in the second material coating may contain residual material stemming from the removal of the first material. Removing subwavelength objects of the first material may include depositing a layer of polymer such as polydimethylsiloxane (PDMS), or an adhesive, and manually peeling the polymer layer or adhesive layer from the substrate along with the subwavelength objects of the first material. The surface may also be washed with a solvent. Or, the surface may be mechanically scraped to remove the coated template particles. Removal of the subwavelength objects of the first material leaves the mesh ("fish-net") coating on the substrate. The mesh structure forms as the second material is deposited in the voids of the template or scaffold.

In some embodiments, the subwavelength coating may exhibit a plasmonic response in which the coating includes nano-sized or micron-sized objects of a polymer or a ceramic as a first material, and a second material comprised of a metal such as silver, aluminum, or gold, a material with a metal-insulator transition such a vanadium dioxide, or a semiconductor.

In some embodiments, the subwavelength coating may exhibit a photonic response in which the coating includes nano-sized or micron-sized objects of a polymer or a ceramic as a first material, and a second material comprised of a dielectric polymer, a dielectric ceramic such as titania or alumina, a material with a metal-insulator transition such a vanadium dioxide, or a semiconductor.

Formation of Subwavelength Mesh (Fish-Net) Structures—(II)

Figure 6A:
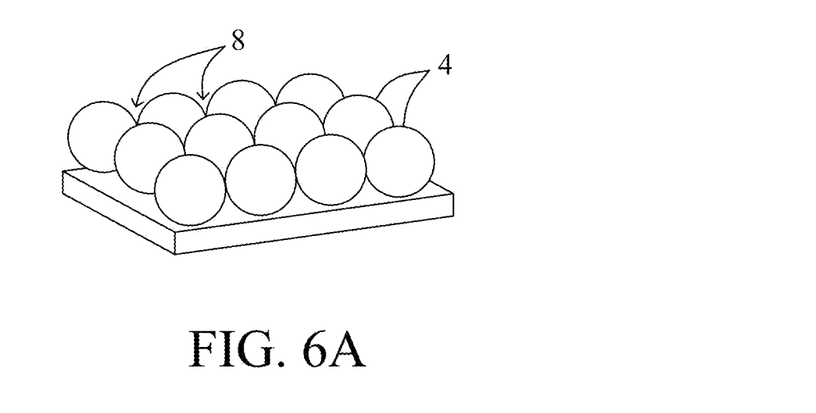
FIGS. 6A-6E show coated structures in the process of FIG. 5.

FIG. 6A illustrates an exemplary template or scaffold 10 on a substrate 2 following a first deposition step in the process of the present invention described previously in reference to FIG. 5. In the figure, the template or scaffold includes nano-sized or micron-sized spheres 4 of a first material [e.g., polystyrene, (PS)] that self-assemble in a close-packing arrangement on the substrate 2. The template includes voids 8 or valleys positioned between the close-packed nanospheres 4. Void sizes are not limited provided the voids are of a subwavelength size.

Figure 6B:
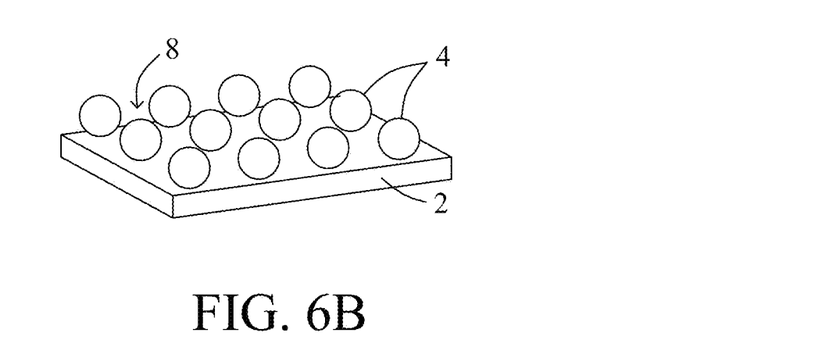

FIG. 6B illustrates the resulting monolayer template or scaffold on the substrate 2 following etching of the nanostructures. Etching the nanospheres in a plasma isotropically reduces the size of the nanospheres, which increases the size of the voids between the nanospheres and changes the close-packed layer to a non-close packed structure.

Figure 6C:
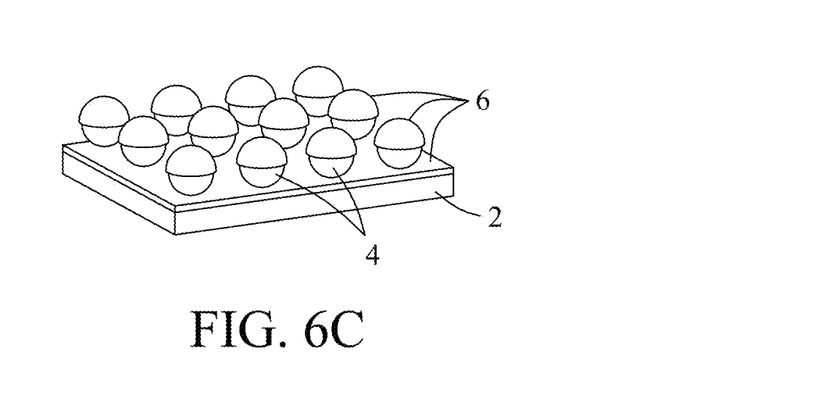

FIG. 6C illustrates the coated substrate 2 following vacuum deposition of the second material 6 comprising a selected metal (e.g., gold or silver) to the substrate 2. onto nanospheres or microspheres 4 previously deposited and between the nanospheres or microspheres 4. The second material 6 may be deposited, for example, via vacuum-sputter deposition onto nanospheres or microspheres 4 that form the template or scaffold on substrate 2. As shown in the figure, the selected metal (second) material 6 coats both the nanospheres or microspheres 4 and voids or open spaces between the nanospheres or microspheres 4 on the substrate 2. The metal coating 6 may include a thickness between about 10 nm to about 35 nm on average. However, no limitations are intended.

Figure 6D:
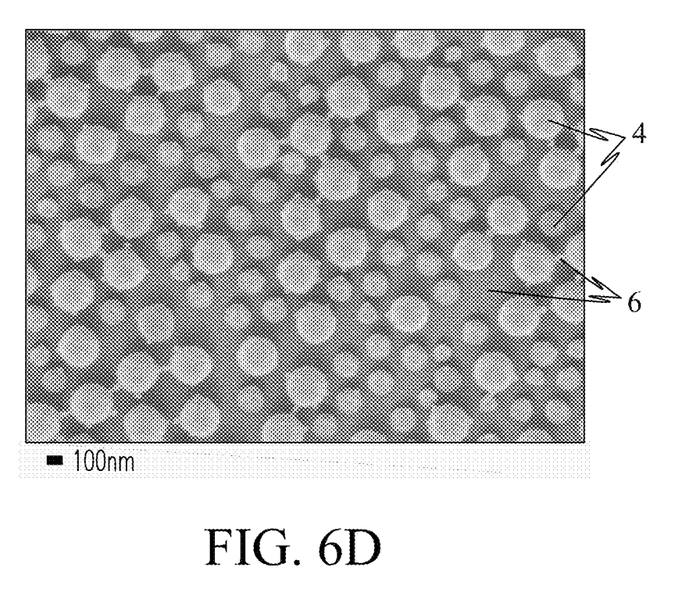

FIG. 6D is an SEM image showing a coated substrate following vacuum deposition of a selected (second material) metal onto silica (first material) nanospheres or microspheres previously deposited to the substrate. Particles in the figure have a poly-modal size distribution with at least two different average sizes or diameters.

Figure 6E:
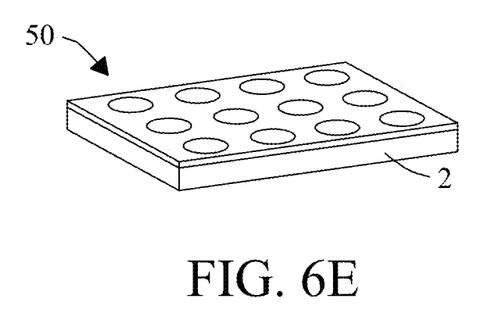

FIG. 6E illustrates the resulting subwavelength mesh coating formed following removal of sacrificial template nanospheres.

Figure 7:
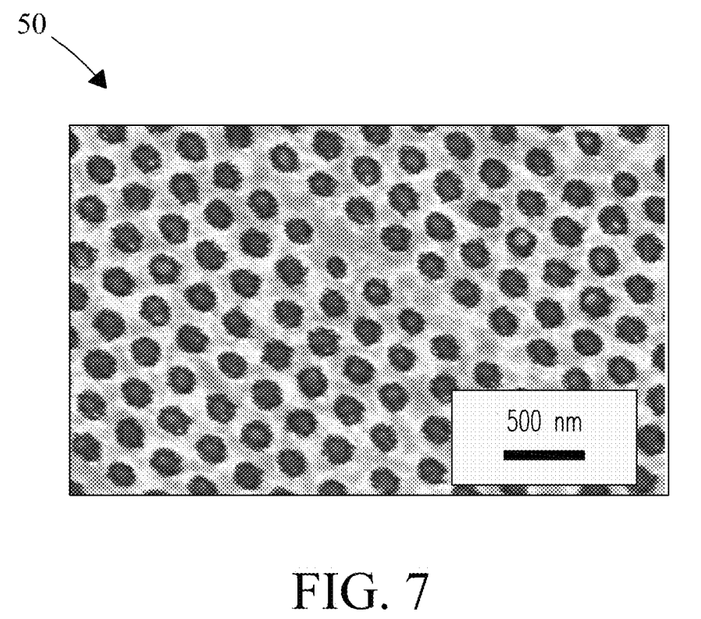
FIG. 7 is an SEM image showing an exemplary subwavelength coating prepared in accordance with one embodiment of the present invention.

FIG. 7 is an SEM image showing a representative subwavelength mesh coating including the characteristic quasi-periodic pattern of subwavelength features. The subwavelength coating also includes a substantially uniform, non-limiting thickness.

Figure 8:
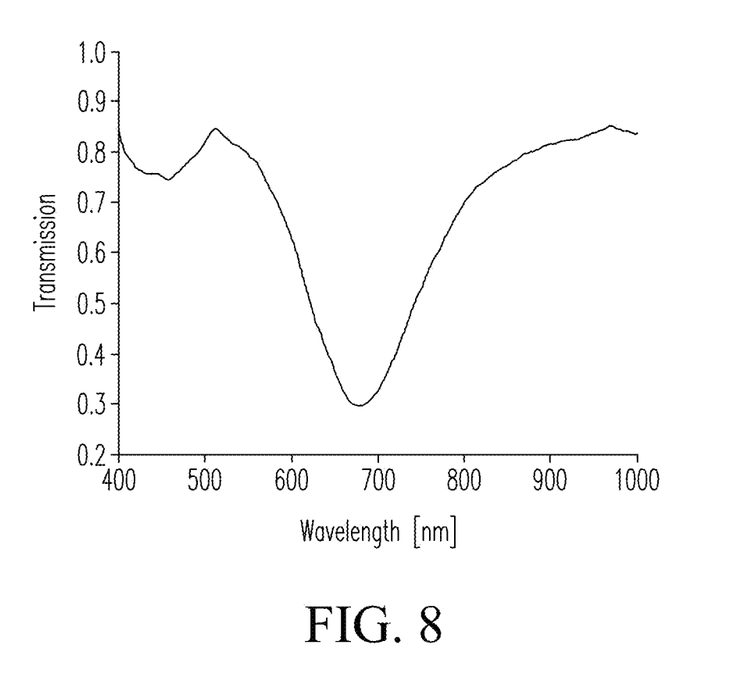
FIG. 8 plots transmission values of an exemplary subwavelength (photonic) coating of the present invention.

FIG. 8 plots transmission values of an exemplary subwavelength (photonic) mesh coating of the present invention formed by vacuum metal deposition of the second material. As shown in the figure, the subwavelength coating with its quasi-periodic pattern exhibits a resonant drop in transmission. In the figure, for example, the coating exhibits a characteristic resonance at about 675 nm. Such resonance behavior can be tailored for selected applications based on choices of the first and second materials and other factors including, but not limited to, for example, particle size and coating thickness.

Advantages

The present invention is a low-cost process for preparation of plasmonic and photonic subwavelength coatings. Processes of the present invention are scalable permitting coverage of both small and large substrates useful during manufacturing and suitable for both energy management and light-management applications.

In some embodiments, the coated area may be on the scale of at least about a square meter or greater.

In some embodiments, coatings may be formed in a continuous fashion over at least about 100 feet in length.

Wet deposition of the present invention also significantly reduces fabrication costs compared to conventional lithography known in the art that renders coatings of the present invention suitable for mass production.

Applications

Coatings of the present invention find application in, for example, energy efficient windows for buildings; vehicle windows; dynamic IR thermal management and control; paints for IR thermal management; building or vehicle envelope (e.g., roofing and wall) materials for radiative cooling applications; down-conversion coatings for waveguides and scintillators; coatings for solar power applications; directional photonic coatings for high intensity light-emitting diodes (LED's); thermal control applications; aerospace applications; sensors; visible and infrared light management; superlenses; plasmon polaritons; optics; electromagnetic applications; gradient-index materials; thermal energy management applications; scattering, redirection, and manipulation of visible light.

While exemplary embodiments of the present invention have been shown and described, it will be apparent to those skilled in the art that many changes and modifications may be made without departing from the invention in its true scope and broader aspects. The appended claims are therefore intended to cover all such changes and modifications as fall within the spirit and scope of the invention.

What is claimed is:

1. A method of forming a subwavelength plasmonic mesh coating, comprising the steps of:
   depositing a first material comprising dielectric particles of a subwavelength size onto a substrate that self-assemble thereon forming a monolayer template with subwavelength voids between the dielectric particles;
   etching the dielectric particles to reduce the size thereof and increase the size of the subwavelength voids between the dielectric particles in the monolayer template;
   coating the monolayer template with a second material comprising a metal selected from Ag, Au, Al, or combinations thereof to substantially fill the subwavelength voids therein;
   heating the monolayer template at a temperature from about 100° C. to about 300° C. for a time sufficient to sinter the second metal material therein forming a continuous and substantially periodic metal mesh between the dielectric particles in the subwavelength voids; and
   removing the dielectric particles from the monolayer template to form the subwavelength plasmonic metal mesh coating on the substrate.

2. The method of claim 1, wherein the substrate includes a glass, a ceramic, or a polymer.

3. The method of claim 1, wherein depositing the first material includes delivering a liquid solution containing the dielectric particles with a delivery device positioned a selected distance above the surface of the substrate to obtain a substantially uniform coverage of the dielectric particles in the monolayer template.

4. The method of claim 1, wherein coating the second material includes delivering a liquid solution containing the metal as metal particles of a selected size with a delivery device positioned a selected distance above the surface of the substrate.

5. The method of claim 1, wherein coating the second metal material is performed via magnetron sputter deposition or thermal evaporation deposition.

6. The method of claim 1, wherein coating the second material includes a second material comprising the metal and a material with a metal-insulator transition or a semiconductor.

7. The method of claim 1, wherein the depositing and coating steps are performed with a roller-based coating method.

8. The method of claim 1, wherein the dielectric particles are non-spherical.

9. The method of claim 1, wherein the dielectric particles include a size selected from about 20 nm to about 500 nm such that the plasmonic metal mesh coating has a resonant absorption, reflection, or transmission with wavelengths of electromagnetic radiation in the UV, visible, or infrared spectrum.

10. The method of claim 1, wherein the dielectric particles include a size selected from about 1 micron to about 15 microns such that the plasmonic metal mesh coating has a resonant absorption, reflection, or transmission with wavelengths of electromagnetic radiation in the infrared spectrum.

* * * * *